US00PP13783P29

(12) United States Plant Patent
Hofmann

(10) Patent No.: US PP13,783 P2
(45) Date of Patent: May 6, 2003

(54) VARIETY OF GERANIUM PLANT NAMED 'PACTOMGIMEX'

(75) Inventor: Christa Hofmann, Grossdittmannsdorf (DE)

(73) Assignee: Elsner Pac Jungpflanzen (DE)

( * ) Notice: Subject to any disclaimer, the term of this patent is extended or adjusted under 35 U.S.C. 154(b) by 0 days.

(21) Appl. No.: 10/118,266

(22) Filed: Apr. 8, 2002

(51) Int. Cl.[7] ..... A01H 5/00
(52) U.S. Cl. ..... Plt./332
(58) Field of Search ..... Plt./332

*Primary Examiner*—Kent Bell
(74) *Attorney, Agent, or Firm*—Webb Ziesenheim Logsdon Orkin & Hanson, P.C.

(57) ABSTRACT

A new and distinct ivy geranium plant having distinct bi-colored flowers of burgundy and white and leaves with heart-shaped zones.

1 Drawing Sheet

VARIETAL DENOMINATION

'Pactomgimex'.

CLASSIFICATION

*Pelargonium×peltatum* (ivy geranium).

BACKGROUND OF THE INVENTION

The present invention comprises a new and distinct cultivar of geranium known by the varietal name 'Pactomgimex'. The new variety was discovered following embryo rescue and grafting in a selective breeding program in Dresden, Germany. The new variety is the result of a combination breeding of unnamed, unpatented selections from breeding group Peltatum dark (group 7j embryo rescue). Plants of the new variety exhibit trailing like their heritage, but differ in having semi-double to double, two-colored flowers. The new variety was first asexually reproduced by cuttings in Dresden, Germany in 2000. The new variety has been trial and field tested and has been found to retain its distinctive characteristics and remain true to type through successive propagations.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions by cuttings carried out in Dresden, Germany. Plants described were about 9 months old. The color readings were taken on plants grown in pots in greenhouses during summer. Color references are primarily to The R.H.S. Colour Chart of The Royal Horticultural Society of London.

PLANT

Form: Trailing.
Height from media surface to top of foliage: 12–15 cm.
Height from media surface to top of umbels: 20–23 cm.
Growth: Well-branched, hanging.

Roots: White, adventive, 4 weeks to develop.
Time to produce a flowering plant: 3 months.
Leaves: Opposite arrangement; heart-shaped zone.
*Length.*—3.5 cm.
*Width.*—7 cm.
Shape:
*Overall.*—Ivy-shaped. Base: Cordate. Apex: Pointed.
Margin: Entire.
Texture: Hairy.
Color:
*Upper surface.*—137B with zone of 137A.
*Lower surface.*—147B.
Ribs and veins:
*Venation.*—Net-veined.
*Color.*—147C.
Petioles:
*Color.*—147B.
*Length.*—2–4 cm.
Stem/branches:
*Color.*—147B.
*Overall stem length.*—55–60 cm.
*Internode length.*—2.5–3 cm.
*Lateral branch length.*—45–50 cm.

THE BUD

When just beginning to open:
Shape:
*Overall.*—Umbel-shaped.
*Individual bud.*—Shell-shaped.
Color: 46B.
Size:
*Cluster.*—4.5 cm in diameter.
*Individual bud.*—Length 1.2 cm. Width: 0.8 cm.

INFLORESCENCE

Flowering: Continuous through summer until frost.
Borne: Umbel; flower on pedicel, pedicel on peduncle.
Umbel:
*Width.*—8–9 cm.
*Depth.*—4 cm.
*Number of flowers per umbel.*—7–9.
*Lastingness.*—4–6 weeks.

Flowers:

*Form.*—Zygomorph, semi-double to double.

*Size.*—Diameter: 5–6 cm. Depth: 1.5 cm.

*Petals.*—Color: Upper surface: 53A at margin, 49D in middle. Lower surface: 46B at margin, 49D in middle. Quantity: 28, including petaloids. Size: Length: 2.1 cm. Width: 1.2 cm. Shape: Overall: Oval. Apex: Round. Base: Pointed. Margin: Entire. Texture: Velvety.

Petaloids:

*Quantity.*—13.

*Shape.*—Irregular.

*Color.*—53A to 46B and 49D (both surfaces).

Sepals:

*Shape.*—Overall: Narrow, linear. Apex: Pointed. Base: Fused.

*Color.*—Upper Surface: 137D. Lower Surface: 137D.

*Size.*—Length: 1.4 cm. Width: 0.3 cm.

Pedicel:

*Length.*—3 cm.

*Color.*—137B.

Peduncle:

*Length.*—11 cm.

*Color.*—137D.

Disease/pest resistance: No susceptibility to diseases or pests noted to date.

REPRODUCTIVE ORGANS

Stamens:

Anthers.—2 mm long.

*Filaments.*—Length: 7 mm. Color: 59D.

*Pollen.*—28A.

Pistils:

*Number.*—One, five parted.

*Length.*—3 mm.

*Stigma.*—59A.

*Style.*—Length: 3 mm. Color: 60D.

*Ovaries.*—Superior, hairy. Length: 0.4–0.6 cm. Color: 138D.

Fruit: If present, maximum 5 per flower, 0.4 cm long, 165A.

GENERAL CHARACTERISTICS

1. Bicolored flowers pattern of velvet burgundy and white.
2. Good branching.
3. High degree of doubleness.
4. Heat tolerant.
5. Large flowers.
6. Heart-shaped zonation.

I claim:

1. A new and distinct variety of geranium plant substantially as shown and described.

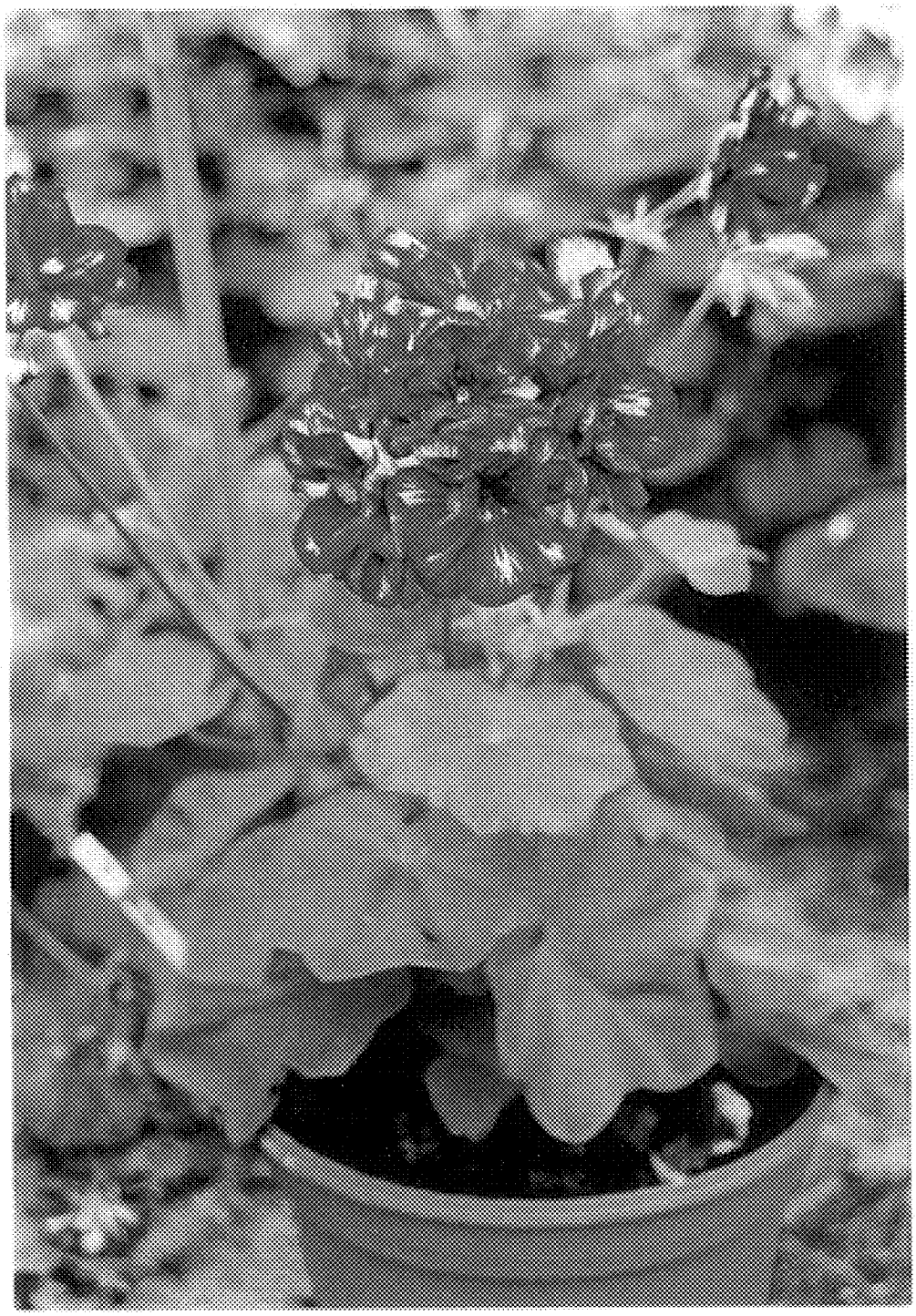

* * * * *